United States Patent

Schmiesing et al.

Patent Number: 5,109,017
Date of Patent: Apr. 28, 1992

[54] (2-THIENYL)ALKYLAMINE DERIVATIVES HAVING NEUROPROTECTIVE PROPERTIES

[75] Inventors: Richard J. Schmiesing; Ronald C. Griffith, both of Pittsford; Robert J. Murray, Rochester, all of N.Y.

[73] Assignee: Fisons Corporation, Rochester, N.Y.

[21] Appl. No.: 589,963

[22] Filed: Sep. 26, 1990

[51] Int. Cl.⁵ .................. A61K 31/38; C07D 333/22
[52] U.S. Cl. ...................... 514/438; 549/77; 514/422; 514/326; 514/397; 546/213; 548/527; 548/336
[58] Field of Search .............. 549/77; 514/438, 422, 514/326, 397; 540/500; 548/527, 336; 546/213

[56] References Cited

FOREIGN PATENT DOCUMENTS 0322582  7/1989  European Pat. Off. ............ 540/500

OTHER PUBLICATIONS

Y. Suzuki et al., *Chemical Abstracts* 99:105648g "Assymetric-substituted Phenethylamines," p. 623 (1983).
*Chemical Abstracts* 100:102914b, "Phenethylamines," p. 609 (1984) Abstract of JP-58-172,350 [83-172,350].

Primary Examiner—Glennon H. Hollrah
Assistant Examiner—Mark W. Russell
Attorney, Agent, or Firm—McAulay Fisher Nissen Goldberg & Kiel

[57] ABSTRACT

Compounds of the formula I,

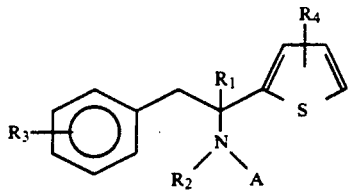

in which:
- $R_1$ represents hydrogen or $C_{1-6}$ alkyl,
- $R_2$ represents hydrogen, $C_{1-6}$ alkyl, $C_{3-6}$ alkenyl, $C_{3-6}$ alkynyl or $C_{3-6}$ cycloalkyl,
- $R_3$ represents one or more radicals selected from hydrogen, hydroxy, $C_{1-6}$ alkyl, $C_{1-6}$ alkoxy, halogen, trifluoromethyl, amino, lower alkylamino or dilower alkylamino,
- $R_4$ represents one or more radicals selected from hydrogen or $C_{1-6}$ alkyl,
- A represents an alpha-amino acid acyl group or an alkoxycarbonyl group, and pharmaceutically acceptable salts thereof are useful as pharmaceuticals, in particular they possess N-methyl-(d)-aspartate (NMDA) blocking properties and are useful in the treatment and/or prevention of neurological disorders such as stroke, cerebral ischaemia, cerebral palsy, hypoglycaemia, epilepsy, Alzheimer's disease, Huntington's chorea, Olivo-ponto-cerebellar atrophy, perinatal asphyxia and anoxia.

9 Claims, No Drawings

(2-THIENYL)ALKYLAMINE DERIVATIVES HAVING NEUROPROTECTIVE PROPERTIES

This invention relates to novel (2-thienyl)alkylamine derivatives, processes for their preparation, pharmaceutical formulations containing them and their neuroprotective properties.

PRIOR ART

European Patent Application, publication number 0322582, discloses, among many other compounds, ortho-substituted alpha-(2-thienyl)benzeneethanamines with anticonvulsant properties.

BACKGROUND

Compounds which possess N-methyl-(d)-aspartate (NMDA) blocking properties are useful in the treatment and/or prevention of neurodegeneration in pathological conditions such as stroke, cerebral ischaemia, cerebral palsy, hypoglycaemia, epilepsy, Alzheimer's disease, Huntington's chorea, Olivo-ponto-cerebellar atrophy, perinatal asphyxia and anoxia.

DETAILED DESCRIPTION

According to the invention we provide compounds of formula I,

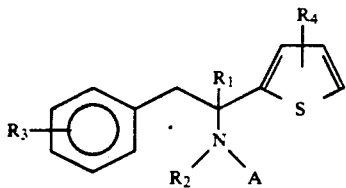

in which:
- $R_1$ represents hydrogen or $C_{1-6}$ alkyl,
- $R_2$ represents hydrogen, $C_{1-6}$ alkyl, $C_{3-6}$ alkenyl, $C_{3-6}$ alkynyl or $C_{3-6}$ cycloalkyl,
- $R_3$ represents one or more radicals selected from hydrogen, hydroxy, $C_{1-6}$ alkyl, $C_{1-6}$ alkoxy, halogen, trifluoromethyl, amino, lower alkylamino or dilower alkylamino,
- $R_4$ represents one or more radicals selected from hydrogen or $C_{1-6}$ alkyl,
- A represents $COC(R_5R_6)N(R_7R_8)$ or $COOC_{1-6}$ alkyl,
- $R_5$ represents hydrogen, $C_{1-6}$ alkyl, hydroxy-$C_{1-2}$ alkyl, mercaptomethyl, (methylthio)$C_{1-2}$ alkyl, carboxy-$C_{1-2}$ alkyl, 2-($C_{1-3}$ alkoxy)ethyl, (aminocarbonyl)$C_{1-2}$ alkyl, amino-$C_{1-4}$ alkyl, 3-imidazolylmethyl, phenylmethyl or (4-hydroxyphenyl)methyl or, in addition $R_5$ together with the adjacent nitrogen may represent a piperidine, pyrrolidine or a 2-pyrrolidinone ring,
- $R_6$, $R_7$ and $R_8$ independently represent hydrogen or $C_{1-6}$ alkyl, or, in addition $R_7$ and $R_8$ taken together with the nitrogen to which they are attached may represent a $C_{4-5}$N heterocyclic ring, or pharmaceutically acceptable acid addition salts thereof.

Pharmaceutically acceptable acid addition salts of the compounds of formula I include salts of mineral acids, for example, hydrohalic acids, e.g. hydrochloric or hydrobromic; or organic acids, for example, formic, acetic or lactic acids. The acid may be polybasic, for example sulphuric, fumaric, maleic or citric acid.

Certain compounds of formula I may exist in different stereoisomeric forms, including optical enantiomeric forms. All are included within the scope of the invention.

According to another aspect of the invention, there is provided a process for the preparation of the compounds of formula I or pharmaceutically acceptable salts thereof, which comprises (a) producing a compound of formula I in which A represents COC $(R_5R_6)N(R_7R_8)$, by reacting the corresponding compound of formula I in which A represents hydrogen with a compound of the formula II,

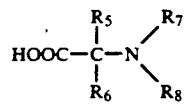

or a carboxyl activated derivative thereof, in which $R_5$, $R_6$, $R_7$ and $R_8$ have the same meaning as defined above provided that, in addition, when one or both of $R_7$ and $R_8$ are hydrogen then at least one of $R_7$ and $R_8$ represents a nitrogen protecting group; or (b) producing a compound of formula I in which A represents $COC(R_5R_6)N(R_7R_8)$, by reacting the corresponding compound of formula I in which A represents $COC(R_5R_6)X$ and X represents a suitable leaving group with a corresponding amine of the formula $HNR_7R_8$; or (c) producing a compound of the formula I in which A represents $COOC_{1-6}$ alkyl by reacting the corresponding compound of formula I in which A represents hydrogen with the corresponding $C_{1-6}$ alkyl haloformate; or (d) producing a compound of formula I containing one or more amino or hydroxy groups by removing a protecting group from a compound of formula I in which one or more of the amino or hydroxyl groups is protected;

and where desired or necessary converting the resulting compound of formula I into a pharmaceutically acceptable salt thereof or vice versa.

The condensation of process a) may be carried out in conditions similar to those used for the synthesis of peptide bonds in protein chemistry, e.g. by carrying out the reaction in the presence of N,N'-carbonyldiimidazole in a polar aprotic solvent or using a hindered base, e.g. triethylamine and an alkyl chloroformate. When one or both of $R_7$ and $R_8$ represents H, the N atom of the compound of formula II requires protection. One particularly suitable protecting group is benzyloxycarbonyl, which may readily be removed by hydrogenolysis or hydrogen bromide in acetic acid. Other groups that may be mentioned include t-butyloxycarbonyl, (Boc), which is removed by standing the peptide in cold trifluoroacetic acid; Fmoc, which may be removed by treatment with dilute piperidine (20% in DMF); (4-methoxybenzyl)oxycarbonyl and 2-nitrophenylsulphenyl. Further protecting groups and methods for their removal are decribed in T W Greene, Protective Groups in Organic Synthesis, Wiley-Interscience, 1981. When both $R_7$ and $R_8$ represent alkyl the condensation may also be carried out by reacting with the acid chloride of the compound of formula II with the corresponding compound of formula I.

In the reaction of process (b), suitable leaving groups represented by X include halogen, preferably chlorine or bromine, alkyl- or arylsulfonate radicals, for example methyl sulfonate or p-toluene sulfonate. The amination reaction may be carried out in the absence of a solvent or in the presence of suitable solvent, for example, ethanol or methylene chloride. The reactions may be carried out at a temperature of, for example, from $-80°-100°$ C.

In the reaction of process (c), suitable halogens include chlorine, bromine and iodine, suitable haloformate esters include, for example, methyl or ethyl chloroformate. Conventional acylation techniques for amines may be used, for example, the reactions may be carried out in a suitable inert solvent, for example, toluene, methylene chloride or tetrahydrofuran. The reactions may be carried out in the presence of a base, and at a temperature of, for example, from $0°-100°$ C.

In the reaction of process (d), removal of the protecting group depends on the nature of the protecting group and includes acidic or basic cleavage or hydrogenolysis. Suitable amine protecting groups are, for example, ethoxycarbonyl, benzyloxycarbonyl, t-butyloxycarbonyl or $C_{1-3}$ alkanoyl.

Acid addition salts of compounds of formula I may be converted to the corresponding free-base by the action of a stronger base. The acid addition salts of the compound of formula I may be prepared by reaction of the free base with an appropriate acid.

The starting materials for the products of reactions (a) and (c) are either well known or may be prepared from compounds known per se by conventional methods or by modifications thereof as described in the examples. The following references provide methods for their preparation;

European Patent Application, publication number 0322582; Mrongovius et al (Chem Abs. 96(5), 28273x); Takahashi et al (Chem. Abs. 99(13), 105648q); and Japanese Kokai 58172350(abstracted in Chem. Abs 100(13), 102914b).

The starting materials for the products of reaction (c) may be prepared from the compounds of formula I in which A is hydrogen by conventional acylation techniques by reaction with an activated carboxylic acid derivative which contains a leaving group alpha to the carbonyl group, for example, chloracetyl chloride or 2-bromopropionylchloride, in the presence of an acid acceptor, for example, triethylamine or pyridine.

In the compound of formula I;

alkyl groups which $R_1$, $R_2$, $R_3$, $R_4$, $R_5$, $R_6$, $R_7$ and $R_8$ may represent include methyl, ethyl, propyl, isopropyl, n-butyl, iso-butyl and s-butyl;

alkenyl groups which $R_2$ may represent include 2-propenyl, 2-butenyl and 2-methyl-2-propenyl;

alkynyl groups which $R_2$ may represent include 2-propynyl and 2-butynyl;

cycloalkyl groups which $R_2$ may represent include cyclopropyl, cyclobutyl, cyclopentyl and cyclohexyl;

alkoxy groups which $R_3$ may represent include methoxy, ethoxy and propoxy;

halogen groups which $R_3$ may represent include fluorine, chlorine, bromine or iodine;

heterocyclic rings which $R_7$ and $R_8$ together with the nitrogen to which they are attached may represent include pyrrolidine and piperidine;

by lower alkyl we mean $C_{1-6}$ alkyl;

amino acids which A may represent include glycine, alanine, leucine, proline, methionine, serine and sarcosine.

We prefer compounds of formula I or a pharmaceutically acceptable salt thereof, in which;

$R_1$ represents hydrogen, methyl, ethyl or isopropyl, preferably hydrogen or methyl;

$R_2$ represents hydrogen, methyl, ethyl or isopropyl, preferably hydrogen or methyl;

$R_3$ represents hydrogen, hydroxy, amino or chloro, preferably hydrogen or amino;

$R_4$ represents hydrogen or methyl;

A represents $COC(R_5R_6)N(R_7R_8)$, methoxycarbonyl or ethoxycarbonyl;

$R_5$ represents hydrogen or $C_{1-6}$ alkyl preferably hydrogen or methyl;

$R_6$ represents hydrogen or $C_{1-6}$ alkyl preferably hydrogen or methyl;

$R_7$ represents hydrogen or $C_{1-6}$ alkyl preferably hydrogen, methyl or ethyl;

$R_8$ represents hydrogen or $C_{1-6}$ alkyl preferably hydrogen, methyl or ethyl;

We especially prefer compounds in which $R_3$ is hydrogen.

We especially prefer compounds in which $R_4$ is methyl.

A sub-group of compounds which are preferred are those in which A is $COCH_2NH_2$.

Certain compounds of formula I, and their pharmaceutically acceptable acid addition salts are useful because they possess pharmacological activity in animals.

The compounds have useful neuroprotective properties. In particular they possess NMDA blocking properties. Neurodegeneration is known to be caused or accelerated by certain excitatory amino acids found naturally in the central nervous system (CNS). Glutamate is an endogenous amino acid which has been characterized as a fast excitatory transmitter in the mammalian brain. Glutamate is also known as a powerful neurotoxin capable of killing CNS neurons under certain pathologic conditions which accompany stroke and cardiac arrest. It has been shown that the sensitivity of central neurons to hypoxia and ischemia can be reduced by the specific antagonism of post synaptic glutamate receptors. Glutamate is characterized as a broad spectrum agonist having activity at four neuronal excitatory amino acid receptor sites. These receptor sites are named after the amino acids which selectively excite them: kainate (KA), N-methyl-D-aspartate (NMDA), 2-amino-4-phosphonobutyrate (APB) and quisqualate (QUIS). Glutamate is believed to be a mixed agonist capable of binding to and exciting all four receptor types. Thus agents which selectively block or antagonise the action of glutamate at these receptors can prevent neurotoxic injury associated with anoxia, hypoxia or ischemia. In particular, compounds which bind to the NMDA receptor site and selectively block the action of glutamate are useful in the prevention and treatment of neurodegenerative diseases.

In addition, certain compounds of formula I demonstrate anticonvulsant activity by their ability to inhibit maximal electroshock (MES) induced seizures in mice; certain compounds inhibit the onset of convulsions and death induced by administration of NMDA to mice; and certain compounds demonstrate antihypoxia activity by their ability to increase the survival time of mice in an oxygen depleted environment.

Antiepileptic activity may be measured by assessing a compound's ability to prevent the hind limb tonic extension component of the seizure in groups of mice induced by maximal electroshock (MES) after oral or intraperitoneal administration according to the procedures of the Epilepsy Branch, NINCDS as published by R. J. Porter, et al., *Cleve. Clin. Quarterly* 1984, 51, 293, and compared to the standard agents dilantin and phenobarbital. Activities ($ED_{50}$'s) in the range of 10-400 m/k after oral administration in this assay system were obtained.

Certain compounds of this invention may possess useful antihypoxia activity. This activity may be conveniently measured in mice. Groups of mice are tested at various times after the intraperitoneal administration of graded doses of the test compound. The animals' survival time in a temperature controlled hypoxic environment (96% nitrogen and 4% oxygen) is recorded. A statistical comparison is made between coincident vehicle treated animals and the experimental group. The dose-response and minimum active dose (MAD) for compounds are obtained. Other modes of administration can also be used.

NMDA activity may be measured in several ways;

a) NMDA blocking activity is measured by assessing a compound's ability to protect mice from convulsions induced by intravenous administration of 150 m/k of NMDA according to the procedures of Czuczwar et al., (Neurotransmitters, Seizures and Epilepsy III, edited by G. Nistico et al., Raven Press, New York 1986, pages 235-246). Groups of mice are pretreated by 30 min with the test compound by the oral or intraperitoneal routes and then given NMDA. Animals were observed for convulsions as defined by loss of righting reflex and appearance of tonic/clonic seizures. Animals are kept for 60 min after NMDA dosing and mortality was recorded.

b) NMDA receptor antagonist activity is measured in vitro by assaying a compounds ability to inhibit binding of the ion-channel, non-competitive receptor antagonist 10,11-dihydro-5-methyl-5H-dibenzo[a,d]-cyclohepten-5,10-imine(MK801) to its receptor. The method is described by Foster and Wong, Br. J. Pharmacol. 91, 403-409 (1987). Briefly, crude brain membrane is prepared by homogenizing rat brain cortex and hippocampus in ice cold 0.32M sucrose. The homogenate is centrifuged and the resulting pellet is lysed by resuspending in ice cold distilled water. The membrane is collected by centrifugation and frozen at −70 C for at least 18 hours. On the day of assay the membrane pellet is thawed and resuspended in 5 mM Tris-acetate at room temperature. The suspension is allowed to incubate at room temperature for 20 mins. and then collected by centrifugation. This process of suspension, incubation and centrifugation is repeated four times. The assay is carried out at room temperature for 45 mins. in a total volume of 1 mL containing 5 mM Tris-acetate, 2 nM [3H]MK801 and test compound and 0.5 mL of membrane suspension under four conditions: a) added buffer, b) added 1 μM glycine, c) added 1 μM glutamate, and d) added 10 μM of both. The nonspecific binding is determined in the presence of 100 μM cold MK801. The reaction is terminated by rapid filtration through Whatman GF/B filter. The specific MK801 binding is defined as the total binding minus the binding in presence of 100 μM cold MK801.

Under these conditions, antagonists acting at the glycine site inhibit [3H]MK801 binding alone or in the presence of glutamate, are partially reversed by 1 uM glycine (an agonist), and completely reversed by the high concentration of a glutamate and glycine mixture. Competitive glutamate antagonists inhibit [3H]MK801 binding alone or in the presence of added glycine, are partially reversed by added glutamate (an agonist), and completely reversed by high concentrations of glutamate and glycine. Noncompetitive antagonists, which interact at the MK801 site inhibit [3H]MK801 binding under all conditions.

c) NMDA and glycine receptor affinity may also be tested in the [3H]L-glutamate and [3H]glycine binding assays following the method of Monaghan & Cotman, PNAS, 83, 7532, (1986) and Watson et al, Neurosci. Res. Comm., 2, 169, (1988).

For the above-mentioned uses the dosage administered will, of course, vary with the compound employed, the mode of administration and the treatment desired. However, in general, satisfactory results are obtained when the compounds are administered at a daily dosage of from about 0.1 mg to about 20 mg per kg of animal body weight, preferably given in divided doses 1 to 4 times a day or in sustained release form. For man the total daily dose is in the range of from 5 mg to 1,400 mg more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, and pharmaceutically acceptable acid addition salts thereof, may be used on their own or in the form of appropriate medicinal preparations for enteral or parenteral administration.

According to the invention, there is also provided a pharmaceutical composition comprising preferably less than 80% and more preferably less than 50% by weight of a compound of formula I, or a pharmaceutically acceptable salt thereof, in admixture with a pharmaceutically acceptable adjuvant, diluent or carrier.

Examples of such adjuvants, diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include tablets, capsules and dragees;

Sustained release compositions include those in which the active ingredient is bound to an ion exchange resin which is optionally coated with a diffusion barrier to modify the release properties of the resin.

We prefer the composition to contain up to 50% and more preferably up to 25% by weight of the compound of formula I, or of the pharmaceutically acceptable derivative thereof.

The compounds of formula I and pharmaceutically acceptable acid addition salts thereof have the advantage that they are less toxic, more efficacious, are longer acting, have a broader range of activity, are more potent, produce fewer side effects, are more easily absorbed or have other useful pharmacological properties, than compounds of similar structure.

The invention is illustrated, but in no way limited, by the following examples.

PREPARATION OF INTERMEDIATES

Preparation 1

α-(3-Methyl-2-thienyl)benzeneethanamine hydrochloride

To a stirred solution of 50 g (0.40 mol) of 3-methyl-2-thiophenecarboxaldehyde in 150 ml of dry tetrahydrofuran at 0° C. was added dropwise 476 ml (0.47 mol) of a 1M solution of lithium bis(trimethylsilyl)amide in tetrahydrofuran over a 2 hour period. After stirring the mixture an additional 20 minutes at 0° C., 476 ml (0.47 mol) of a 1M solution of benzyl magnesium chloride in diethyl ether was added dropwise over a 2 hour period. The resulting mixture was allowed to warm to ambient temperature, stirred for 0.5 h longer, and poured into 2.5 L of saturated aqueous ammonium chloride. The mixture was extracted with chloroform (3×500 ml), organic layers combined, dried over $MgSO_4$, and concentrated to dryness giving 85 g of the title amine as an oil. A sample of the product (4 g) was dissolved in isopropanol, made acidic with hydrogen chloride in isopropanol, decolorized with carbon, and reconcentrated to near dryness. The crude hydrochloride salt was recrystallized from a solvent mixture of ethyl acetate and methanol to give 2.5 g of white solid (mp 184°–186° C.).

Preparation 2

α-(2-Thienyl)benzeneethanamine hydrochloride

Following essentially the same procedure but substituting 2-thiophene carboxaldehyde for the 3-methyl-2-thiophenecarboxaldehyde in Preparation 1 gave α-(2-thienyl)benzeneethanamine hydrochloride (mp 232°–233° C.).

Preparation 3

N-Methyl-α-(3-methyl-2-thienyl)benzeneethanamine hydrochloride

To a stirred two-phase mixture of 10 g (0.047 mol) of α-(3-methyl-2-thienyl)benzeneethanamine and 7.4 g (0.07 mol) of sodium carbonate in 150 ml of dichloromethane and 200 ml of water at 0° C. was added dropwise 7.6g (0.07 mol) of ethyl chloroformate. The resulting mixture was allowed to warm to ambient temperature and stirred vigorously overnight. The layers were separated, aqueous phase extracted with $CH_2Cl_2$ (2×50 ml), organic layers were combined and washed with 1N aqueous hydrochloric acid, brine, and dried. The crude N-carbethoxy-α-(3-methyl-2-thienyl)benzeneethanamine thus obtained was purified by silica gel chromatography to give 13.3 g of a pale yellow oil. A solution of 7.5 g (0.026 mol) of the oil in tetrahydrofuran (50 mL) was added dropwise to a stirred solution of 22 ml (0.075 mol) of a 3.4M solution of sodium bis (2-methoxyethoxy)aluminum hydride in toluene (Red-AL) dissolved in 150 ml of tetrahydrofuran at ambient temperature. The mixture was stirred overnight and quenched by dropwise addition of isopropanol until bubbling had ceased followed by dropwise addition of water until a white precipitate formed. After stirring for 30 minutes longer, the clear yellow solution was decanted and concentrated to dryness giving the crude product as an oil. The oil was dissolved in 50 ml of isopropanol, chilled to 0° C., and made acidic with hydrochlorinated isopropanol. The resulting white solid was collected by filtration and freeze-dried from water to give 1.8 g of white solid product (mp 214°–216° C.).

Preparation 4

N-Methyl-α-(2-thienyl)benzeneethanamine hydrochloride

Following essentially the same procedure as described in Preparation 3 but substituting α-(2-thienyl)-benzeneethanamine for the α-(3-methyl-2-thienyl)benzeneethanamine results in the preparation of N-Methyl-α-(2-thienyl)-benzeneethanamine hydrochloride (mp 159°–161° C.).

Preparation 5

N-Ethyl-α-(3-methyl-2-thienyl)benzeneethanamine hydrochloride

To a stirred solution of 10 g (0.047 mol) of α-(3-methyl-2-thienyl)benzeneethanamine in 50 ml of pyridine at ambient temperature was added dropwise 6.6 ml (0.07 mol) of acetic anhydride. Mixture was allowed to stand overnight, diluted with 500 ml of ETOAC, washed with 1N HCl until acidic, water, brine and dried. The resulting dark oil obtained from concentration of the organics was purified by chromatography on silica gel to give 8.2 g (0.032 mol) of N-acetoxy-α-(3-methyl-2-thienyl)benzeneethanamine as a light brown solid. To a stirred suspension of this solid in 45 ml of THF at 0° C. was added dropwise 64 ml (0.064 mol) of a 1.M solution of borane in THF. The resulting mixture was allowed to warm to ambient temperature and stirred overnight. The reaction was quenched by carefully adding 100 ml of 6N HCl and was then warmed at 75° C. for 40 hours. The mixture was cooled, made basic with 50% aqueous NaOH, and extracted with $CH_2Cl_2$ (3×200 ml). The organic extracts were combined, washed with water, brine, and dried. The resulting oil obtained from concentration of organics was dissolved in 50 ml isopropanol and made acidic with hydrochlorinated isopropanol. The white solid was collected by filtration and dried giving 5. g of product as a white solid (mp 226°–228° C.).

Preparation 6

N-Ethyl-α-(2-thienyl)benzeneethanamine hydrochloride

By following essentially the same procedure as described in Preparation 5 but substituting; α-(2-thienyl)-benzeneethanamine, α-methyl-α-(2-thienyl)benzeneethanamine, or α-methyl-α-(3-methyl-2-thienyl)benzeneethanamine for the α-(3-methyl-2-thienyl)benzeneethanamine results in the preparation of; N-ethyl-α-(2-thienyl)benzeneethanamine hydrochloride (mp 228°–230° C.), N-ethyl-α-methyl-α-(2-thienyl)benzeneethanamine hydrochloride (mp 191.5°–193° C.), or N-ethyl-α-methyl-α-(3-methyl-2-thienyl)benzeneethanamine hydrochloride mp 189°–192° C.

Preparation 7

α-methyl-α-(2-thienyl)benzeneethanamine hydrochloride a) α-Methyl-α-(2-thienyl)benzenepropanoic acid To an ice-cooled solution of 2-thiopheneacetic acid (30 g, 0.211 mol) in THF (300 mL) was added dropwise n-butyl lithium (275 mL of a 1.6M solution in hexane). The ice-bath was removed and the reaction was stirred for 1 hour. The reaction mixture was again cooled to 0°

C. and hexamethylphosphoramide (34.5 mL) was added dropwise. After 45 minutes a solution of methyl iodide (13.1 mL, 0.211 mol) in THF (75 mL) was added dropwise. The reaction was stirred to room temperature for 45 minutes, recooled to 0° C., n-butyl lithium (1 eq) was added and after 45 minutes a solution of benzyl bromide (36 g, 0.211 mol) in THF (75 mL) was added. After stirring for 3 days the reaction was quenched with 1N.HCl (400 mL). The reaction mixture was partitioned between ethyl acetate and aqueous HCl and the ethyl acetate layer was separated, washed with water, and dried ($MgSO_4$). Concentration of the ethyl acetate afforded an oil which was chromatographed on silica gel and eluted with 40% ethyl acetate/hexanes to give the title product as an oil (63 g).

b) α-methyl-α-(2-thienyl)benzeneethanamine hydrochloride

The acid from step (a) (25 g, 0.102 mol) was dissolved in THF(390 mL) and triethylamine (14.1 mL) was added. Diphenylphosphoryl azide (23.4 mL) was added and the mixture was heated at 65° C. for 5 hours. The reaction was cooled to room temperature and 2,2,2-trichloroethanol (46.1 mL) was added portionwise and then the reaction was heated to reflux for 40 hours. The reaction was cooled to 0° C. and water (40 mL), glacial acetic acid (360 mL) and zinc dust (132 g) were added. The ice bath was removed and the reaction was stirred overnight. After filtration of the reaction mixture through a bed of celite the filtrate was concentrated and the residue was dissolved in ethyl acetate (800 mL). The ethyl acetate was washed with 1N.NaOH (800 mL) and water (800 ml). The ethyl acetate layer was separated, dried ($MgSO_4$) and concentrated to dryness. The residual oil was converted to the hydrochloride salt with ethanolic hydrogen chloride and precipitated by the addition of diethyl ether. A 1 g portion of the hydrochloride was recrystallized from ethyl acetate(20 mL)/MeOH(5 mL)/hexanes(15 mL) to give the title compound (0.8 g), mp 205°-206° C.

Preparation 8

α-methyl-α-(3-methyl-2-thienyl) benzeneethanamine maleate

By following esentially the same procedure as described in Preparation 7 but substituting 3-methyl-2-thiopheneacetic acid for 2-thiopheneacetic, acid results in the preparation of α-methyl-α-(3-methyl-2-thienyl)benzeneethanamine maleate, mp 174°-178° C.

PREPARATION OF EXAMPLES

Example 1

Preparation of
N-methyl-N-[1-(3-methyl-2-thienyl)-2-(2-aminophenyl)ethyl]-2-aminoacetamide dihydrochloride To an ice-cooled solution of N-(benzyloxycarbonyl)-glycine (or CBZ-glycine) (9.31 g, 0.045 mol), N-hydroxysuccinimide (5.12 g, 0.045 mol), and a catalytic amount of 4-(dimethylamino)pyridine in dry THF (100 mL) was added dropwise a solution of dicyclohexylcarbodiimide in THF (75 mL). After 2 hours the reaction was filtered and the filtrate was added to N-methyl-α-(3-methyl-2-thienyl)-2-nitrobenzene-ethanamine(4.1 g, 0.0148 mol). The reaction mixture was stirred overnight at room temperature. The reaction mixture was concentrated and the residue was suspended in ethyl acetate and the insolubles were filtered. Concentration of the ethyl acetate afforded the crude CBZ-glycine derivative which was purified by chromatography on silica gel and elution with 30% ethyl acetate-hexane to give a syrup (5 g). The syrup (5 g) was dissolved in glacial acetic acid (200 mL) and hydrogenated over 5% Pd/C at 40-50 psi for 16 hours. The catalyst was filtered off, a second charge of 5% Pd/C was added and the hydrogenation was continued for 24 hours. Filtration of the catalyst and concentration of the solvent afforded the crude diamine which was converted to the hydrochloride salt in isopropanol-ether to give the title product (1.2 g), mp. 175°-178° C. (decomp.)

Example 2

N-[1-(3-methyl-2-thienyl)-2-phenylethyl]-2-aminoacetamide hydrochloride

To a stirred solution of 13.5 g (0.06 mol) of N-carbobenzyloxyglycine and 7.5 g (0.06 mol) of N-hydroxysuccinimide in 100 ml of dry tetrahydrofuran at 0° C. was added dropwise a solution of 13.3g (0.06 mol) of dicyclohexylcarbodiimide in 50 ml of tetrahydrofuran. The resulting mixture (white solid forms) was allowed to warm to ambient temperature and stirred overnight. To the filtrate obtained after filtering off the white solid was added, with stirring at ambient temperature, a solution of 14 g (0.06 mol) of α-(3-methyl-2-thienyl)benzeneethanamine in 75 ml of tetrahydrofuran over a 30 minute period. The resulting mixture was stirred overnight and concentrated to near dryness to give an oil. Purification by silica gel chromatography gave 15 g of the N-CBZ intermediate as a pale yellow solid. A solution of the solid in 300 ml of glacial acetic acid with 16.5 g of 5% Pd/C catalyst was subjected up to 40 psi. of hydrogen in a Parr apparatus for 24 hours. The mixture was filtered through celite and the filtrate concentrated to near dryness using a toluene azeotrope. The resulting amber colored syrup was partitioned between chloroform (0.5 L) and half-saturated aqueous sodium bicarbonate, the organic layer was washed with water and brine, and dried over sodium sulphate. Concentration of the organic solvents to dryness gave 8 g of crude amine as a syrup, which was dissolved in isopropanol, acidified with hydrogen chloride in isopropanol, and allowed to stand. The solid was collected and recrystallized from isopropanol to give 2.5 g of the hydrochloride as a white solid (mp 229°-232° C.).

Example 3

By following essentially the same procedure as described for Example 2 but substituting; N-methyl-α-(3-methyl-2-thienyl)benzeneethanamine; N-ethyl-α-(2-thienyl)benzeneethanamine; or N-ethyl-α-(3-methyl-2-thienyl)benzeneethanamine for the α-(3-methyl-2-thienyl)benzeneethanamine results in the preparation of; N-methyl-N-[1-(3-methyl-2-thienyl)-2-phenylethyl]-2-aminoacetamide (Z)-2-butenedioate (1:2) salt (mp 128°-130° C.); N-ethyl-N-[1-(2-thienyl)-2-phenylethyl]-2-aminoacetamide (Z)-2-butenedioate (1:1) salt (mp 134°-138° C.); or N-ethyl-N-[1-(3-methyl-2-thienyl)-2-phenylethyl]-2-aminoacetamide (Z)-2-butenedioate (1:1.5) salt (mp 110°-112° C.).

Example 4

N-[1-(2-thienyl)-2-phenylethyl]-2-aminoacetamide maleate a) N-[1-(2-thienyl)-2-phenylethyl]-2-chloroacetamide A solution of chloroacetyl chloride (4 mL, 0.05 mol) in chloroform (40 mL) was added dropwise to a solution of α-(2-thienyl)benzeneethanamine (10 g, 0.049 mol) and triethylamine (14 mL, 0.098 mol) in chloroform (180 mL) at 0° C. The mixture was stirred to room temperature for 1 hour. Dilute HCl (300 mL of 0.75N) was added and the reaction mixture was partitioned. The chloroform layer was separated, dried (MgSO₄) and concentrated to give the amide as a light brown solid (11 g).

b) N-[1-(2-thienyl)-2-phenylethyl]-2-aminoacetamide maleate

The amide (7 g, 0.025 mol) from step (a), dissolved in ethanol (100 mL) was charged to a bomb and cooled to −78° C. Liquid ammonia (25 mL) was added and the sealed bomb was heated at 75°-80° C. overnight. The reaction was purified by chromatography on ammoniated silica gel and elution with 5%MeOH/CHCl₃ to give the product as an oil (3.5 g). The oil was dissolved in absolute ethanol (50 mL) and made acidic with maleic acid (1.9 g). The precipitated solid (2.8 g) was dried at 75° C. for 4 hours to give the title compound, mp 165°-166° C.

Example 5

By following essentially the same procedure as described for Example 4 but substituting, α-methyl-α-(3-methyl-2-thienyl)benzeneethanamine, or α-methyl-α-(2-thienyl)benzeneethanamine for the α-(2-thienyl)benzeneethanamine results in the preparation of N-[1-methyl-1-(3-methyl-2-thienyl)-2-phenylethyl]-2-amino acetamide fumarate, mp 199°-201° C., or N-[1-methyl-1-(2-thienyl)-2-phenylethyl]-2-aminoacetamide maleate, mp 174°-175° C.

What we claim is:

1. A compound of the formula I,

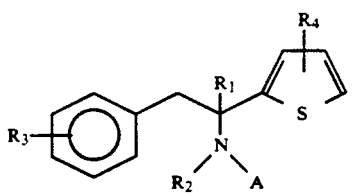

in which:
$R_1$ represents hydrogen or $C_{1-6}$ alkyl,
$R_2$ represents hydrogen, $C_{1-6}$ alkyl, $C_{3-6}$ alkenyl, $C_{3-6}$ alkynyl or $C_{3-6}$ cycloalkyl,
$R_3$ represents one or more radicals selected from hydrogen, hydroxy, $C_{1-6}$ alkyl, $C_{1-6}$ alkoxy, halogen, trifluoromethyl, amino, lower alkylamino or dilower alkylamino,
$R_4$ represents one or more radicals selected from hydrogen or $C_{1-6}$ alkyl,
A represents $COC(R_5R_6)N(R_7R_8)$ or $COOC_{1-6}$ alkyl,
$R_5$ represents hydrogen, $C_{1-6}$alkyl, hydroxy-$C_{1-2}$alkyl, mercaptomethyl, (methylthio)$C_{1-2}$alkyl, carboxy-$C_{1-2}$alkyl, 2-($C_{1-3}$alkoxy)ethyl, (aminocarbonyl)$C_{1-2}$alkyl, amino-$C_{1-4}$alkyl, 3-imidazolylmethyl, phenylmethyl or (4-hydroxyphenyl)methyl or, in addition $R_5$ together with the adjacent nitrogen may represent a piperidine, pyrrolidine or a 2-pyrrolidinone ring,
$R_6$, $R_7$ and $R_8$ independently represent hydrogen or $C_{1-6}$ alkyl, or, in addition $R_7$ and $R_8$ taken together with the nitrogen to which they are attached may represent a $C_{4-5}N$ heterocyclic ring, or
pharmaceutically acceptable acid addition salts thereof.

2. A compound according to claim 1 in which A is represented by $COC(R_5R_6)N(R_7R_8)$.

3. A compound according to claim 2 in which $R_5$, $R_6$, $R_7$ and $R_8$ are selected from hydrogen or $C_{1-6}$ alkyl.

4. A compound according to claim 2 in which $R_1$ and $R_2$ are selected from hydrogen or methyl.

5. A compound according to claim 3 in which $R_5$, $R_6$, $R_7$ and $R_8$ are hydrogen.

6. A compound according to claim 2 in which $R_3$ is hydrogen and $R_4$ is methyl.

7. A compound according to claim 1 which is,
N-methyl-N-[1-(3-methyl-2-thienyl)-2-(2-aminophenyl)-ethyl]-2-aminoacetamide,
N-[1-(3-methyl-2-thienyl)-2-phenylethyl]-2-aminoacetamide,
N-methyl-N-[1-(3-methyl-2-thienyl)-2-phenylethyl]-2-aminoacetamide,
N-ethyl-N-[1-(2-thienyl)-2-phenylethyl]-2-aminoacetamide,
N-ethyl-N-[1-(3-methyl-2-thienyl)-2-phenylethyl]-2-aminoacetamide,
N-[1-(2-thienyl)-2-phenylethyl]-2-aminoacetamide,
N-[1-methyl-1-(3-methyl-2-thienyl)-2-phenylethyl]-2-aminoacetamide, or
N-[1-methyl-1-(2-thienyl)-2-phenylethyl]-2-aminoacetamide, or
a pharmaceuticaly acceptable acid addition salt thereof.

8. A method of treatment of neurological disorders, which method comprises administering to a patient suffering from that disorder an effective amount of one or more compounds of formula I, as defined in claim 1.

9. A pharmaceutical composition comprising a compound of formula I, as defined in claim 1, in admixture with a pharmaceutically acceptable carrier.

* * * * *